United States Patent [19]
Doyle

[11] Patent Number: 5,810,583
[45] Date of Patent: Sep. 22, 1998

[54] REVERSE PULL, EXTRAORAL DENTAL ASSEMBLY WITH HEAD AND BODY SUPPORTS

[75] Inventor: Walter A. Doyle, Lexington, Ky.

[73] Assignee: RMO, Inc., Denver, Colo.

[21] Appl. No.: 608,488

[22] Filed: Feb. 28, 1996

[51] Int. Cl.$^6$ ............................................. A61C 3/00
[52] U.S. Cl. .................................................. 433/5
[58] Field of Search .................... 433/5, 18, 24; 428/97.1, 857, 859, 861; 602/17, 18

[56] References Cited

U.S. PATENT DOCUMENTS

| | | | |
|---|---|---|---|
| 2,151,458 | 3/1939 | Allen | 602/17 |
| 2,334,894 | 11/1943 | Atkinson . | |
| 2,681,058 | 6/1954 | Mathues | 602/17 |
| 3,401,457 | 9/1968 | Hickham . | |
| 4,375,962 | 3/1983 | Dewoskin | 433/5 |
| 4,951,655 | 8/1990 | MacMillan et al. | 602/17 |
| 4,988,291 | 1/1991 | Grummons | 433/5 |
| 5,062,415 | 11/1991 | Weatherby et al. | 602/17 |

FOREIGN PATENT DOCUMENTS 2803560  8/1979  Germany ................................. 433/5

OTHER PUBLICATIONS

Advertisement "Heavy Force Face Mask" (Dr. Henri Petit) Great Lakes Orthodontics Laboratories, Inc., Buffalo, New York 14216.

*Primary Examiner*—Ralph Lewis
*Attorney, Agent, or Firm*—Sheridan Ross P.C.

[57] ABSTRACT

A reverse pull, extraoral dental assembly having at least one head support and at least one body support (e.g., disposed outside of the head region of the dental patient). The head support and body support are interconnected by a brace assembly which is displaced outwardly from the frontal region of the dental patient. One and typically two elastics or other appropriate treatment force generating/transfer members extend from the brace assembly to engage one or more of the dental patient's teeth in the upper and/or lower arch to apply a generally mesially directed treatment force thereto, and/or to engage a device which is directly associated with dental patient bone (e.g., an implant or onplant).

41 Claims, 4 Drawing Sheets

REVERSE PULL, EXTRAORAL DENTAL ASSEMBLY WITH HEAD AND BODY SUPPORTS

FIELD OF THE INVENTION

The present invention generally relates to applying generally mesially directed forces to a patient, for instance to treat many types of malocclusions requiring orthopedic advancement of the maxilla and/or mandible or advancement of the dentition and, more particularly, to a reverse pull, extraoral dental assembly which includes at least one head support and at least one body support for "anchoring" a generally mesially directed treatment force exerted on the patient (e.g., one or more upper teeth and/or lower teeth of a patient, directly on patient bone).

BACKGROUND OF THE INVENTION

One type of malocclusion is a Class III which often times involves a maxillary deficiency. A Class III malocclusion is a condition in which the chin of an individual appears to protrude forwardly a disproportionate amount. Class III malocclusions may be due to excessive mandibular growth and/or maxillary deficiency. One method for treating a Class III malocclusion involving a retracted maxilla is to exert a generally mesially directed force on the boney structures of the lower face by engaging the upper arch of the orthodontic patient. These types of force stimulate bone growth to advance the maxilla mesially and/or orthodontically advance the patient's dentition.

Another type of malocclusion is a Class II malocclusion. A Class II malocclusion exhibits a rearward displaced chin or generally underdeveloped jaw. Particularly in younger patients, this type of malocclusion responds well to generally mesially-directed treatment forces.

The above-noted types of mesially-directed forces are typically applied using what may be characterized as a reverse pull assembly. Known reverse pull assemblies allow for the exertion of the generally mesially-directed force on the patient's upper arch or lower arch by providing a plurality of supports on the patient's facial or head region and by including structure which is outwardly displaced from the patient's face to provide a mounting for elastics or other treatment force generating members. These elastics extend from their mounting on the reverse pull assembly under tension and engage the patient's upper or lower arch. In the case where a rigid arch wire or the like is interconnected with the patient's upper or lower teeth, a pair of elastics are typically used to engage opposite sides of the arch undergoing treatment (e.g,. by engaging hooked appliances indirectly attached to bands on the patient's teeth). The tensioned elastics thereby apply a symmetrical, generally mesially-directed force on the patient's arch undergoing treatment to attempt to achieve the noted objectives, while the corresponding generally distally directed forces are exerted on the patient at the various facial or head supports.

SUMMARY OF THE INVENTION

The present invention generally relates to a reverse pull, extraoral dental assembly which utilizes at least one frontal support on the facial region of the dental patient and at least one frontal support on the body region or outside of the facial region of the dental patient. At least one of the frontal supports on the facial region of the dental patient is interconnected with at least one of the frontal supports disposed outside of the facial region of the dental patient by a brace assembly. The brace assembly is displaced outwardly from the "front" of the dental patient and includes at least one appropriate mount. Elastics or other appropriate force generating/transmitting members engage a mount and extend into the patient's mouth, for instance to engage one or more of the patient's teeth to apply the generally mesially-directed force to the teeth which may be used to affect movement of the dentition and/or to stimulate bone growth. The assembly may also be connected directly to the bone of the upper and/or lower jaws with implants in the bone or "onplants" which are on the bone and under the periosteum, and therefore capable of applying these forces more directly to the bone. Other means include an acrylic palatal appliance or other palate or mandible-engaging functional appliances. That is, the present invention and its ability to transmit generally mesially-directed forces to a dental patient may be used to affect a pure orthodontic treatment, a pure orthopedic treatment, and for combinations thereof.

In one embodiment, at least one frontal support is provided for engaging a portion of the dental patient's forehead and is disposed substantially on or symmetrically relative to the dental patient's vertical midline (i.e., a vertical reference plane which bisects the dental patient). At least one other frontal support is provided for engaging a frontal portion of the dental patient's body, such as at or near the sternum region, and is also disposed substantially on or symmetrically relative to the dental patient's vertical midline. The brace assembly is also thereby substantially coplanar with the dental patient's vertical midline. Both the facial and body supports may be a single support or, alternatively, two or more displaced supports (e.g., disposed symmetrically relative to the noted vertical midline).

Various features which may be incorporated in the reverse pull, extraoral dental assembly of the present invention will be discussed in relation to the above-described embodiment. For instance, the brace assembly may include upper and lower braces which are telescopingly interconnected to accommodate bowing-like movements of the dental patient's head. Relatedly, the brace assembly may be interconnected with the frontal supports in a manner which does not significantly impede other types of movements of the dental patient's head (e.g., by pivotally interconnecting the two ends of the brace assembly with the two frontal supports and also allowing the brace assembly to swivel relative to the same), but which yet still maintains the brace assembly in a position which allows for the continued application of a generally symmetrical force to the dental patient during treatment (e.g., to keep the brace assembly on the patient's vertical midline). Moreover, the positioning of the mount(s) on the brace assembly may be adjusted to accommodate physical differences between dental patients and/or to allow for changing the orientation of the vector of the forces being applied to the dental patient undergoing treatment (e.g., to allow an attending orthodontist to exert a more "downwardly" directed mesial force on the dental patient's upper arch than is typically utilized).

DETAILED DESCRIPTION

Figure 1:
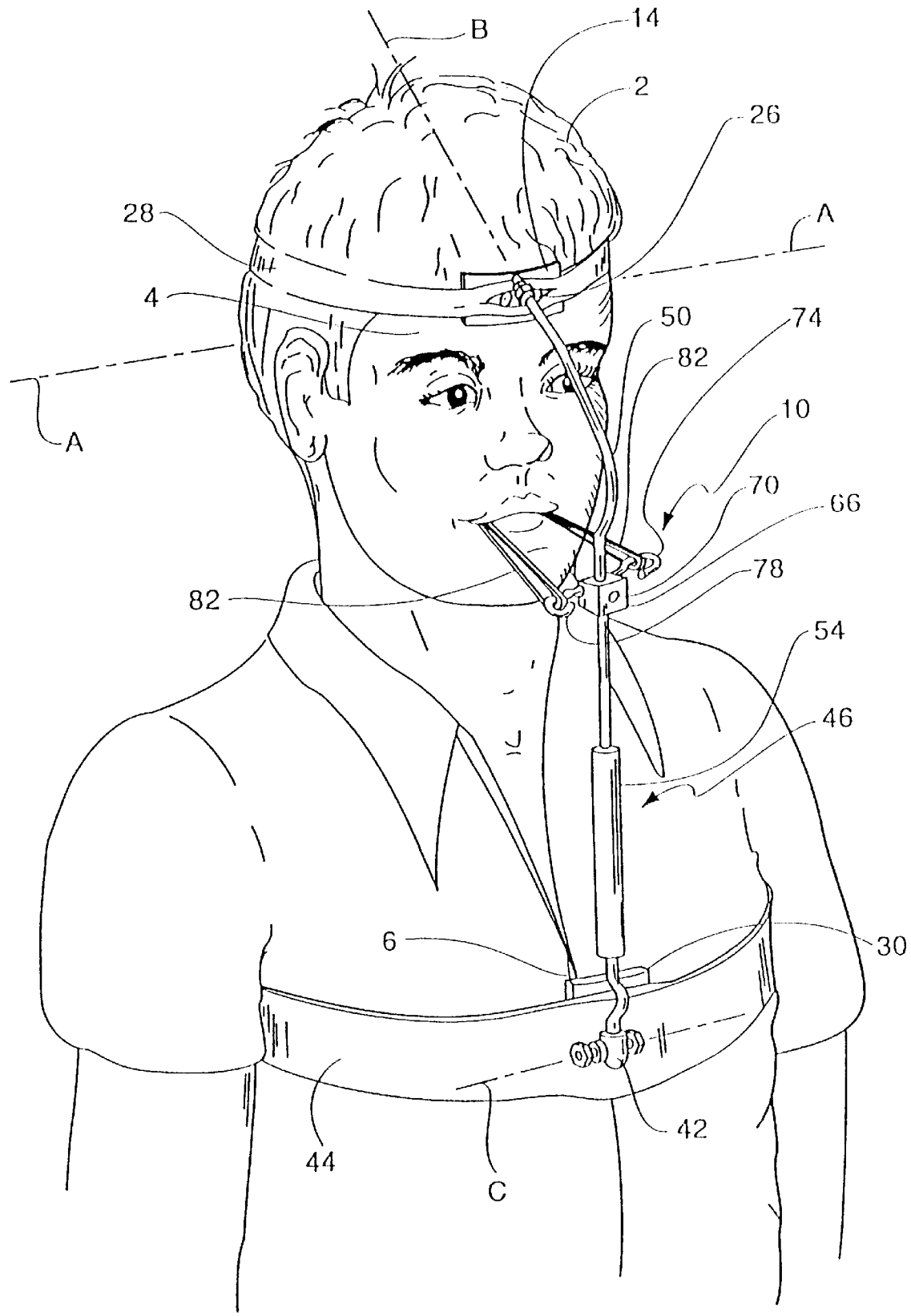
FIG. 1 is a perspective view of one embodiment of a reverse pull, extraoral dental assembly, in accordance with principles of the present invention, being worn by a dental patient.
Figure 2:
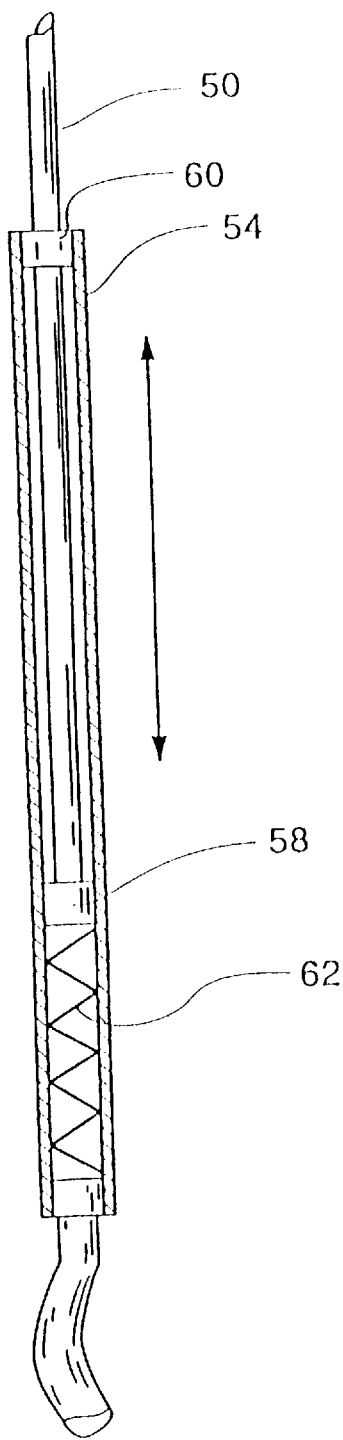
FIG. 2 is a cross-sectional view of a lower portion of the brace assembly of FIG. 1.

The present invention will be described in relation to the accompanying drawings which assist in illustrating its various pertinent features. A reverse pull, extraoral dental assembly 10 is disclosed in FIGS. 1–2 which may be used for a variety of treatments which require the application of a generally mesially-directed treatment force to a dental patient (e.g., typical malocclusions such as Class II and Class III malocclusions), although the assembly 10 accommodates for the application of this force at an angle relative to the occlusal plane. The assembly 10 may be used for orthopedic treatments or treatments which involve moving and/or stimulating the growth of bone, and/or for orthodontic treatments which involve the movement of the dentition (e.g., the assembly 10 may be used to provide a pure orthodontic treatment, a pure orthopedic treatment, or a combination thereof).

The assembly 10 may be interconnected with one or more teeth of the upper arch of the orthodontic dental patient 2, one or more teeth of the lower arch, and/or one or more teeth of both arches simultaneously to affect the desired treatment, and/or bone engaging means as described above. This type of interconnection may be used to stimulate bone growth and/or affect movement of the dentition. That is, the assembly 10 may be interconnected with the dental patient in this manner to affect a pure orthopedic treatment, a pure orthodontic treatment, and to simultaneously affect an orthopedic treatment and an orthodontic treatment. The assembly 10 may also be connected directly to the bone of the upper or lower jaws with implants in the bone or "onplants" which are on the bone and under the periosteum, and therefore capable of applying these forces more directly to the bone. Other means for establishing an interconnection include an acrylic palatal appliance or other palate or mandible-engaging functional appliances. The assembly 10 may also be used in a variety of types of treatments, such as for treating the above-noted malocclusions, for distraction, i.e., the orthopedic pulling of broken bones to encourage growth during healing, and for use during sagittal palatal expansion.

The assembly 10 includes an upper support 14 which engages the forehead 4 of the dental patient 2 and a lower support 30 which engages the body of the dental patient 2, typically in the upper sternum region 6. The upper support 14 and the lower support 30 are interconnected by a brace assembly 46 which is disposed outwardly from the frontal region of the dental patient 2. As such, elastics 82 or other force generating members may extend from the brace assembly 46 to the dental patient 2 to apply the above-described type of generally mesially-directed orthopedic and/or orthodontic treatment force. The lower support 30 is illustrated as interfacing with a more "upper portion" of the sternum 6, such as between the main body of the sternum and the manubrium which is a more preferred position. It will be appreciated that the lower support 30 could interface with a "lower" portion of the sternum as well, although this is not preferred.

The upper support 14 is generally rigid and may be custom contoured and padded for providing a comfortable interface with the forehead 4 of the dental patient 2. An upper strap assembly 28 (e.g., a pair of velcro straps) is interconnected with the upper support 14 to secure the upper support 14 to the dental patient 2, typically by passing the upper strap assembly 28 about the head of the dental patient 2. The upper support 14 is movably interconnected with the brace assembly 46, specifically the upper brace 50, by an upper connector 26. The upper connector 26 allows for a pivoting of the upper support 14 about the axis A (e.g., a generally vertical pivoting action). Moreover, the upper connector 28 allows for a swiveling of the upper support 14 about the axis B (e.g., about an axis generally normal to the forehead 4).

The lower support 30 is generally rigid and may be contoured and padded for providing a comfortable interface with the sternum region 6 of the dental patient 2. A lower strap assembly 44 (e.g., a pair of velcro straps) is interconnected with the lower support 30 to secure the lower support 30 to the dental patient 2, typically by passing the lower strap assembly 44 about the body of the dental patient 2. The lower support 30 is movably interconnected with the brace assembly 46, specifically the lower brace 54, by a lower connector 42. The lower connector 42 mainly allows for a pivoting of the lower support 30 about the axis C (e.g., a generally vertical pivoting action).

Figure 1A:
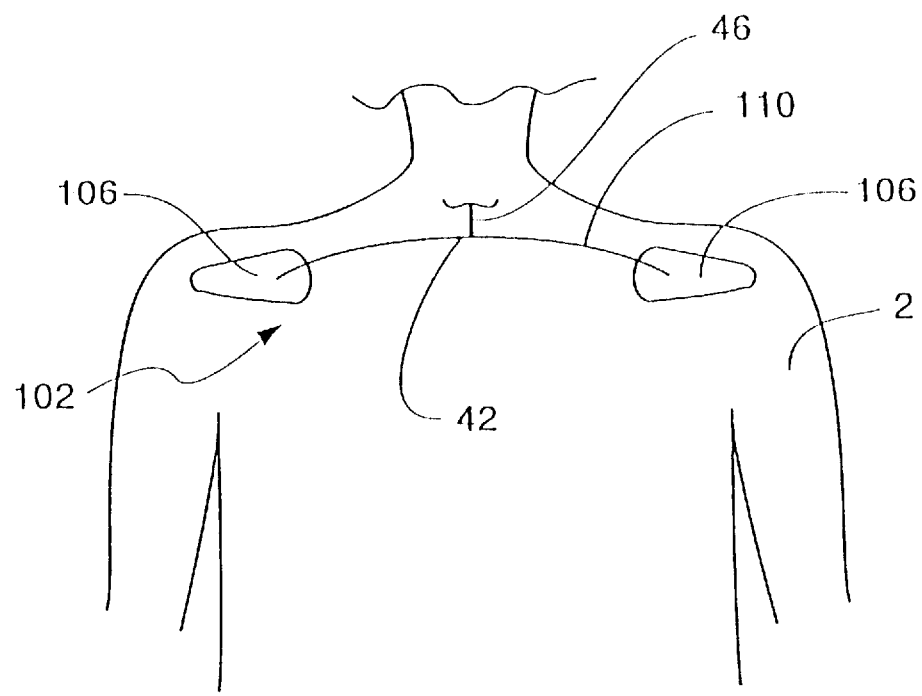
FIG. 1A is a view of another embodiment of a lower or body anchorage for the reverse pull assembly of FIG. 1.

Another embodiment of a lower support which may be used instead of the lower support 30 is illustrated in FIG. 1A. A lower support assembly 102 includes two laterally displaced clavicle engaging supports 106 which are interconnected by a lateral brace 110 and which may be appropriately secured to the dental patient 2. The clavicle engaging supports 102 may be rigidly interconnected with the lateral brace 110 or may be movable relative to the lateral brace 110 to account for certain movements by the dental patient 2. The lower portion of the brace assembly 46 may be interconnected with the lateral brace 110 in the same manner which the brace assembly 46 interconnects with the lower anchorage 30. It should be appreciated that these principles could be applied to the upper support 14 as well (e.g., using a pair of laterally displaced head-engaging supports positioned equidistant from the vertical midline of the patient on opposite sides thereof).

The brace assembly 46 interconnects the upper support 14 and the lower support 30 and includes the upper brace 50 and lower brace 54. The upper brace 50 and lower brace 54 are slidably interconnected in a telescopingly-like manner which accommodates for certain movements by the dental patient 2 without adversely affecting the application of the treatment forces to the dental patient 2. A stop 58 is fixedly attached to the lower end of the upper brace 50, is received within the interior of the lower brace 54, and engages a spring 62 which is contained within the lower brace 54 and which is seated in a lower portion of the lower brace 54. The upper brace 50 may then advance further within the lower brace 54 by compressing the spring 62 and may move away from the lower brace 54 which allows for expansion of the spring 62. Moreover, the spring 62 may be sized such that it holds the weight of the assembly 10 neutrally with the head of the dental patient 2 in the level position.

Figure 1B:
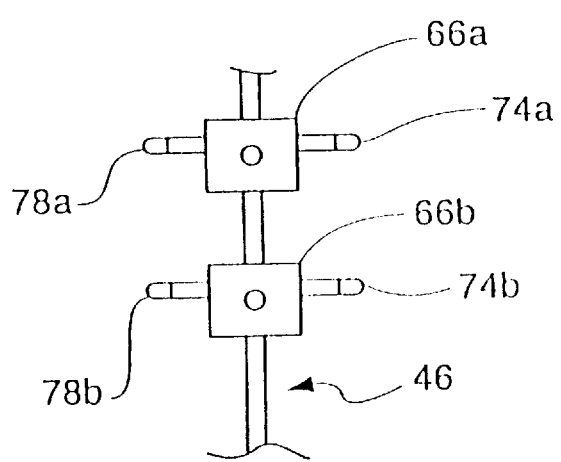
FIG. 1B is a view of another embodiment of a portion of a brace assembly for the reverse pull assembly of FIG. 1.
Figure 1C:
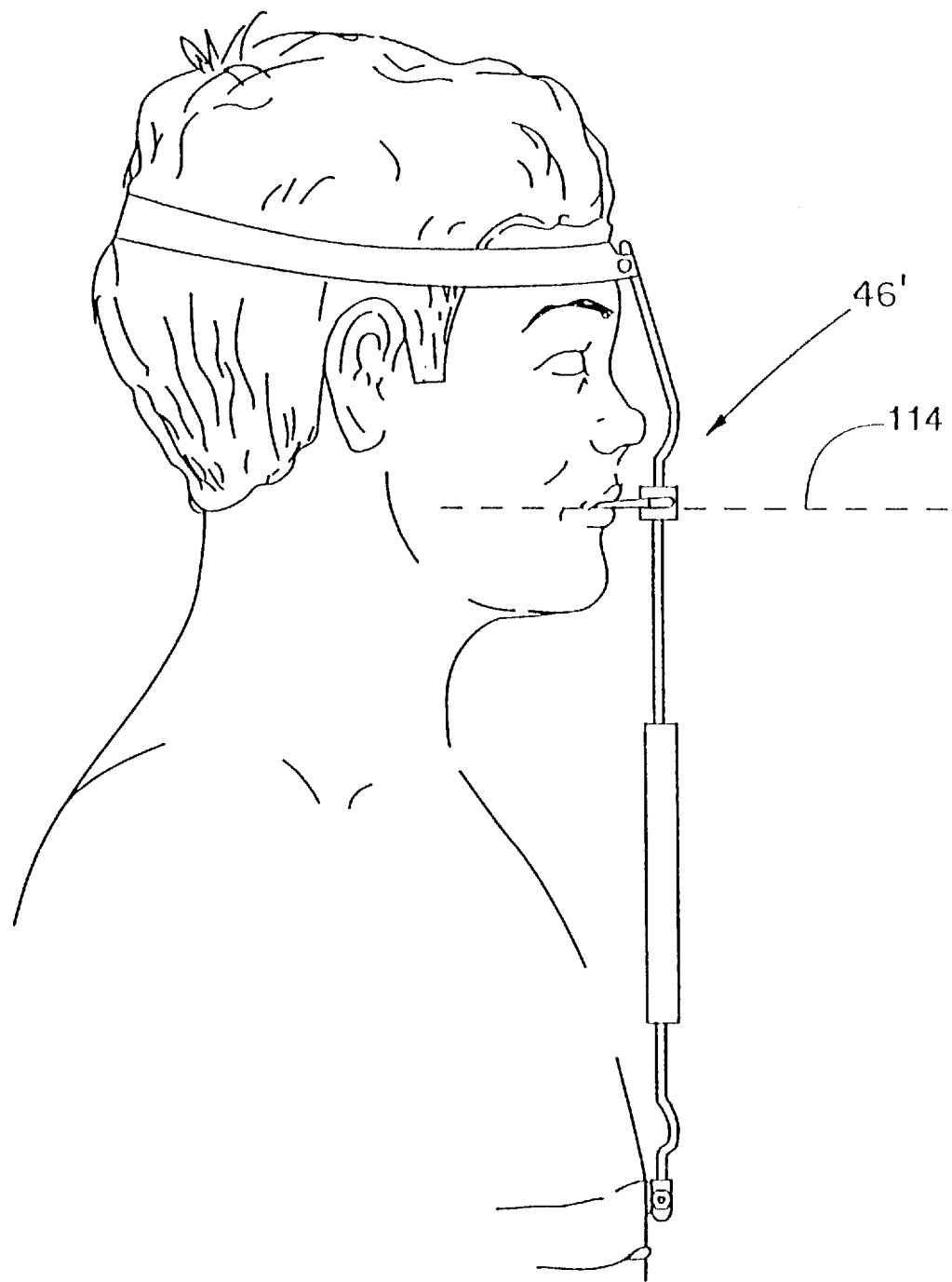
FIG. 1C is a view of another embodiment of a brace assembly for the reverse pull assembly of FIG. 1.

The brace assembly 46 also provides a mounting for the elastics 82 such that the desired generally mesially directed treatment force may be applied to the dental patient 2. In FIG. 1, the brace assembly 46 is presented in a somewhat distorted view to enhance illustration of various features. Typically, it is more desirable for the brace assembly to more closely follow the patient's profile as illustrated in FIG. 1C where the brace assembly 46' is generally about 1 inch in front of the lips of the patient 2.

Referring back to FIG. 1, a mount 66 is disposed on the upper brace 50 and maintains a fixed position relative to the upper brace 50 by the engagement of a set screw 70 against the upper brace 50. The set screw 70 may engage a flat on the upper brace 50 which maintains the assembly 10 in the desired position. Disengagement of the set screw 70 allows the vertical positioning of the mount 66 to be adjusted relative to the upper brace 50 and thus relative to the dental patient 2. This adjustment allows the reverse pull, extraoral dental assembly 10 to be used with a variety of dental patient's having different physical characteristics and/or allows for changing the vector of the treatment force being applied to the dental patient 2 if required for treatment. For instance, in certain situations it may be desirable to apply a more "downwardly" directed force than would typically be used to treat a Class III malocclusion and the assembly 10 allows the practitioner to utilize this type of force. As a general rule, it will be desirable for the mount 66 to be adjustable between positions relative to the upper brace 50 of about ¼ inch above the line of embrasure 114 (FIG. 1C) and about ½ inch below the line of embrasure 114.

The vertically adjustable mount 66 includes a first hook 74 and a second hook 78 for receiving one or more elastics 82. Each elastic 82 extends from one of the hooks 74, 78 and interfaces with the dental patient 2. In the embodiment illustrated in FIG. 1B, two vertically displaced mounts 66 are provided which may be desirable for certain types of treatments (e.g., to allow one elastic to extend from the first hook 74a of the upper mount 66a to the lower arch, one elastic to extend from the second hook 78a of the upper mount 66a to the lower arch, one elastic from the first hook 74b of the lower mount 66b to the upper arch, and one elastic from the second hook 78b of the lower mount to the upper arch).

One way in which the interface between the dental patient 2 and the assembly 10 may be established is by attaching one of the elastics 82 to a hooked appliance, such as a buccal tube, on a band attached to a molar tooth on one side of the dental patient's 2 upper arch, and attaching the other elastic 82 to a hooked appliance, such as a buccal tube, on a band attached to a molar tooth on the other side of the dental patient's 2 upper arch. In the event that the dental patient's 2 teeth of the upper arch are interconnected to all teeth within the arch by a rigid arch wire, a generally mesially directed force is applied to the dental patient's 2 upper arch by the assembly 10. Similarly, generally mesially-directed forces can be applied to the lower arch in this manner. Forces can be simultaneously applied to the upper and lower arches, and different force vectors may be used when two mounts 66 are utilized (FIG. 1B).

The assembly 10 can also be used to move anterior teeth in the dental patient's 2 upper and/or lower arch by selective joining of teeth by the archwire, or by using elastic (82) anchor points on the teeth other than molars. Other known methods of interconnecting elastics with teeth and/or methods of interconnecting the teeth for arch movement and/or movement of the dentition may be utilized than those described herein. Due to the structure of the assembly 10, it should be appreciated that it allows for simultaneous treatment of the upper arch/upper dentition and the lower arch/lower dentition (e.g., due to its stability on the dental patient 2 by using the head and body supports). In this regard, four elastics 82 may be used, two for the upper teeth/arch and two for the lower teeth/arch. The use of two vertically displaced mounts 66 may also be utilized to further augment the direction of forces. Moreover, it should be appreciated that other ways of interfacing the elastics 82 with the dental patient 2 may be utilized depending upon, for instance, the particular treatment to be used with the present invention's ability to apply generally mesially directed forces to the dental patient 2.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A reverse-pull, extraoral dental assembly, comprising:

first means for engaging a portion of a dental patient's head between an occlusal plane of the patient and a crown of the patient's head;

second means for engaging a portion of the dental patient's body spaced from the patient's head;

third means for interconnecting said first and second means for engaging, said third means being generally displaced outwardly from a frontal region of the dental patient;

fourth means, interconnectable with said third means, for anchoring a means for exerting at least a mesially directed force on at least one of the patient's mandible, the patient's maxilla, and at least one tooth of the patient.

2. An assembly, as claimed in claim 1, wherein:
   said first means comprises means for engaging at least a portion of a forehead of the dental patient.

3. An assembly, as claimed in claim 1, wherein:
   said first means comprises at least one forehead support.

4. An assembly, as claimed in claim 1, wherein:
   said second means comprises means for engaging at least a frontal portion of a body of the dental patient.

5. An assembly, as claimed in claim 1, wherein:
   said second means comprises means for engaging a sternum region of the dental patient.

6. An assembly, as claimed in claim 1, wherein:
   said second means comprises a sternum support.

7. An assembly, as claimed in claim 1, wherein:
   said third means comprises a substantially rigid brace assembly.

8. An assembly, as claimed in claim 7, wherein:
   at least a portion of said brace assembly is generally arcuately shaped.

9. An assembly, as claimed in claim 7, wherein:
   at least a portion of said brace assembly is displaced generally outwardly away from the dental patient.

10. An assembly, as claimed in claim 7, wherein:
    said brace assembly is pivotally interconnected with each of said first and second means for engaging.

11. An assembly, as claimed in claim 7, wherein:
    said brace assembly comprises an upper brace and a lower brace, said upper and lower braces being telescopingly interconnected to provide a telescoping action between said upper and lower braces during dental patient movements.

12. An assembly, as claimed in claim 1, wherein:
said third means is disposed within a reference plane which extends through a nose of the dental patient to generally bisect the dental patient's head into mirror images.

13. An assembly, as claimed in claim 1, wherein:
said fourth means is rigidly interconnected with said third means.

14. An assembly, as claimed in claim 1, further comprising:
means for adjusting a vertical position of said fourth means relative to said third means.

15. An assembly, as claimed in claim 1, wherein:
said fourth means is slidably interconnected with said third means.

16. A reverse-pull, extraoral dental assembly, as claimed in claim 1, wherein said means for exerting is capable of exerting a force on the patient's mandible and maxilla simultaneously.

17. A reverse-pull, extraoral dental assembly, as claimed in claim 1, wherein said means for exerting is capable of exerting a force at an angle to an occlusal plane of the dental patient.

18. A reverse-pull, extraoral dental assembly, comprising:
a first frontal support engageable with at least a portion of a forehead of a dental patient;
a second frontal support adapted to be engaged with a portion of the patient's body spaced from the patient's head;
a brace assembly extending between and interconnected with each of said first and second frontal supports; and
a treatment force transfer member mounting interconnected with said brace assembly to allow for applying a force to at least one of the patient's mandible, the patient's maxilla, and at least one tooth of the patient.

19. An assembly, as claimed in claim 18, further comprising:
a strap assembly interconnected with said first frontal support.

20. An assembly, as claimed in claim 18, wherein:
said second frontal support is adapted for engaging at least a portion of a frontal body region of the dental patient.

21. An assembly, as claimed in claim 18, wherein:
said second frontal support is adapted for engaging a sternum region of the dental patient.

22. An assembly, as claimed in claim 18, wherein:
at least a portion of said brace assembly is generally arcuately shaped.

23. An assembly, as claimed in claim 18, wherein:
at least a portion of said brace assembly extends generally mesially away from the dental patient.

24. An assembly, as claimed in claim 18, wherein:
said brace assembly is pivotally interconnected with each of said first and second frontal supports.

25. An assembly, as claimed in claim 18, wherein:
said brace assembly comprises upper and lower telescopingly interconnected braces to provide a telescoping action between said upper and lower braces during dental patient movements.

26. An assembly, as claimed in claim 18, wherein:
said treatment force transfer member mounting is rigidly interconnected with said brace assembly.

27. An assembly, as claimed in claim 18, further comprising:
means for adjusting a vertical position of said treatment force transfer member mounting relative to said brace assembly.

28. An assembly, as claimed in claim 18, wherein:
said treatment force transfer member mounting is slidably interconnected with said brace assembly.

29. An assembly, as claimed in claim 18, further comprising:
at least a second said treatment force member mounting interconnected with said brace assembly.

30. An assembly, as claimed in claim 29, further comprising:
a positional adjustment assembly for at least two of said treatment force member mountings.

31. A reverse-pull, extraoral dental assembly, as claimed in claim 18, wherein said treatment force transfer member mounting allows for applying a force simultaneously to both the patient's mandible and maxilla.

32. A reverse-pull, extraoral dental assembly as claimed in claim 18, wherein said treatment force transfer member mounting allows for applying a force at an angle to an occlusal plane of the patient.

33. A method of orthopedic/orthodontic treatment, comprising:
engaging a frontal head region of a dental patient outside of a jaw region of the dental patient;
engaging a frontal body region of the dental patient spaced from the head of the dental patient;
exerting at least a mesially directed force on at least one of the dental patient's mandible, the dental patient's maxilla, and at least one tooth of the dental patient using both of said engaging steps; and
exerting generally distally directed forces on said frontal head region and said frontal body region from said exerting at least a mesially directed force step.

34. A method of orthopedic/orthodontic treatment as claimed in claim 33, further including a step of adjusting a direction of said mesially directed force when the dental patient's head moves in relation to the frontal body region.

35. A method of treatment as claimed in claim 33, wherein said step of exerting includes exerting a force simultaneously on a patient's mandible and maxilla.

36. A method of treatment as claimed in claim 33, wherein said step of exerting includes exerting a force at an angle to an occlusal plane of the dental patient.

37. A reverse-pull, extraoral dental assembly, comprising:
first means for engaging a portion of a facial region of a dental patient;
second means for engaging a sternum region of the dental patient;
third means for interconnecting said first and second means for engaging, said third means being generally displaced outwardly from a frontal region of the dental patient;
fourth means, interconnectable with said third means, for anchoring means for exerting at least a mesially directed force on at least one of the patient's mandible, the patient's maxilla, and at least one tooth of the patient.

38. A reverse-pull, extraoral dental assembly, comprising:
first means for engaging a portion of a facial region of a dental patient;
second means for engaging a sternum of the dental patient;
third means for interconnecting said first and second means for engaging, said third means being generally displaced outwardly from a frontal region of the dental patient;

fourth means, interconnectable with said third means, for anchoring means for exerting at least a mesially directed force on at least one of the patient's mandible, the patient's maxilla, and at least one tooth of the patient.

39. A reverse-pull, extraoral dental assembly, comprising:

first means for engaging a portion of a facial region of a dental patient;

second means for engaging a portion of the dental patient outside of the facial region;

third means for interconnecting said first and second means for engaging, said third means being generally displaced outwardly from a frontal region of the dental patient and comprising a substantially rigid brace assembly comprising an upper brace and a lower brace, said upper and lower braces being telescopingly interconnected to provide telescoping action between said upper and lower traces during dental patient movements;

fourth means, interconnectable with said third means, for anchoring means for exerting at least a mesially directed force on at least one of the patient's mandible, the patient's maxilla, and at least one tooth of the patient.

40. A reverse-pull, extraoral dental assembly, comprising:

a first frontal support engageable with at least a portion of a forehead of a dental patient;

a second frontal support adapted to be engaged with a sternum region of the dental patient;

a brace assembly extending between and interconnected with each of said first and second frontal supports; and a treatment force transfer member mounting interconnected with said brace assembly to allow for applying a force to at least one of the patient's mandible, the patient's maxilla, and at least one tooth of the patient.

41. A reverse-pull, extraoral dental assembly, comprising:

a first frontal support engageable with at least a portion of a forehead of a dental patient;

a second frontal support engageable with the dental patient outside of a facial region of the dental patient;

a brace assembly extending between and interconnected with each of said first and second frontal supports; and a treatment force transfer member mounting interconnected with said brace assembly to allow for applying a force to at least one of the patient's mandible, the patient's maxilla, and at least one tooth of the patient;

wherein said brace assembly comprises upper and lower telescopingly interconnected braces to provide a telescoping action between said upper and lower braces during dental patient movements.

* * * * *